(12) United States Patent
Tatarkiewicz

(10) Patent No.: US 9,909,972 B2
(45) Date of Patent: Mar. 6, 2018

(54) MULTI-CAMERA APPARATUS FOR OBSERVATION OF MICROSCOPIC MOVEMENTS AND COUNTING OF PARTICLES IN COLLOIDS AND ITS CALIBRATION

(71) Applicant: Jan J. Tatarkiewicz, San Diego, CA (US)

(72) Inventor: Jan J. Tatarkiewicz, San Diego, CA (US)

(73) Assignee: Manta Instruments, Inc., San Diego, CA (US)

( * ) Notice: Subject to any disclaimer, the term of this patent is extended or adjusted under 35 U.S.C. 154(b) by 208 days.

(21) Appl. No.: 15/018,532

(22) Filed: Feb. 8, 2016

(65) Prior Publication Data

US 2017/0227439 A1    Aug. 10, 2017

(51) Int. Cl.
*G06K 9/00*    (2006.01)
*G01N 15/10*    (2006.01)
*G01N 15/14*    (2006.01)

(52) U.S. Cl.
CPC ..... *G01N 15/1012* (2013.01); *G01N 15/1429* (2013.01); *G01N 15/1436* (2013.01); *G06K 9/00* (2013.01)

(58) Field of Classification Search
CPC .............. G03F 9/7053; G03F 7/70775; G03F 7/70716; G03F 7/70725; G03F 7/70233; G03F 7/70258; G03F 7/70283; G03F 7/703; G03F 7/707; G03F 7/70108; G03F 7/705; G03F 9/7015; G03F 9/7049; A61B 18/20; A61B 5/0071; A61B 5/0084; A61B 5/0086; A61B 5/0088; A61B 5/0091; A61B 5/07; A61B 5/412; A61B 5/4547; A61B 17/00491; A61B 17/0057; A61B 17/12022; A61B 17/12118; A61N 2005/0626; A61N 2005/0663; A61N 5/01; A61N 5/0603;
(Continued)

(56) References Cited

U.S. PATENT DOCUMENTS

| 4,008,402 A | * | 2/1977 | O'Keeffe | ............ | H01J 37/3045 |
| | | | | | 219/121.29 |
| 6,274,323 B1 | * | 8/2001 | Bruchez | ................. | B82Y 15/00 |
| | | | | | 435/6.11 |

(Continued)

*Primary Examiner* — Aklilu Woldemariam
(74) *Attorney, Agent, or Firm* — Manuel de la Cerra

(57) ABSTRACT

A system and method are provided to observe and count particles in polydisperse solutions with dark field microscopy while distinguishing among particles of different sizes and accurately counting particles. A calibration mask, calibration light source, and multiple wavelengths of light are used. Opaque calibration marks on the transparent calibration mask define a region of interest. Multiple beams of various wavelengths are combined into a beam or a light sheet and the perpendicular component of scattered light from the specimen particles is then split into separate wavelengths and detected by separate sensors attuned to each wavelength. By calibrating the region of interest and measuring rotational and translational differences between images captured by differing sensors, the images may be aligned exactly and merged, enabling: i) removal of duplicate particles which yields more accurate particle counts, ii) more accurate estimation of the examined volume, and iii) accurate particle concentration measurements.

26 Claims, 8 Drawing Sheets

(58) Field of Classification Search
CPC .............. A61N 5/0624; G01N 2458/00; G01N 2015/0053; G01N 15/0205; G01N 21/6486; G01N 2201/061; G01N 27/447; G01N 27/44756; G01N 33/487; G01N 33/5091; G01N 33/54346; G01N 33/588; G01N 33/533; G01N 30/0005; G01N 15/1425; C03C 23/0025; C03C 3/14; C03C 8/04; C03C 8/18; C03C 8/24; C04B 2235/3206; C04B 2235/3208; C04B 2235/3213; C04B 2235/3215; C04B 2235/3217; C04B 2235/3224; C04B 2235/3286; C04B 2235/3409; G06K 9/00832; G06K 9/00362; G06K 9/00369; G06K 9/00335; G06K 9/00771; G06K 9/4661; B60R 21/0152; B60R 21/01538; B60R 21/01534; B60R 21/01536; B60R 2021/0027; B60R 21/013; B60R 21/0134; G01C 3/06; G01S 17/46; G01S 17/66; G01S 17/89; G01S 3/781; G01S 3/786; G01S 7/4816; B01L 2300/0654; B01L 2300/0829; B01L 2300/0851; B01L 2300/0896; B01L 2300/12; B01L 3/5085; H01B 1/22; Y10T 428/24942; Y10T 428/25; Y10T 428/2991; B29C 64/268; B29C 64/393; B33Y 50/00; B33Y 30/00; B33Y 40/00; B22F 2003/1056; B22F 3/1055; B23K 26/032; B23K 26/0876; B23K 26/342; G01B 11/026; G01B 2290/15; G01B 2290/70; G01B 9/02018; G01B 9/02061; G01B 9/02091

See application file for complete search history.

(56) References Cited

U.S. PATENT DOCUMENTS

| | | | | |
|---|---|---|---|---|
| 7,118,676 | B2* | 10/2006 | Mueth | A61M 1/36 210/729 |
| 7,444,178 | B2* | 10/2008 | Goldbach | G01S 5/16 382/103 |
| 8,778,469 | B2* | 7/2014 | Kawanami | H01J 9/26 313/495 |
| 9,605,363 | B2* | 3/2017 | Zhang | B82Y 10/00 |
| 2001/0046053 | A1* | 11/2001 | Hill | G03F 7/70775 356/496 |
| 2005/0029467 | A1* | 2/2005 | Yu | G02B 21/32 250/442.11 |
| 2006/0003152 | A1* | 1/2006 | Youngs | H01B 1/22 428/212 |
| 2007/0132980 | A1* | 6/2007 | Schoormans | G03F 7/70775 355/72 |
| 2010/0102250 | A1* | 4/2010 | Li | C09K 11/0883 250/459.1 |
| 2010/0261263 | A1* | 10/2010 | Vo-Dinh | A61L 2/08 435/287.1 |
| 2012/0162755 | A1* | 6/2012 | Stroessner | G02B 5/005 359/386 |
| 2017/0122860 | A1* | 5/2017 | Tatarkiewicz | G01N 15/1463 |
| 2017/0341183 | A1* | 11/2017 | Buller | B23K 26/342 |

* cited by examiner US 9,909,972 B2

MULTI-CAMERA APPARATUS FOR OBSERVATION OF MICROSCOPIC MOVEMENTS AND COUNTING OF PARTICLES IN COLLOIDS AND ITS CALIBRATION

TECHNICAL FIELD

The present invention relates to a system for detecting electromagnetic radiation, and more particularly to the observation of nanoparticles in liquid samples using a microscope equipped with digital video cameras/sensors.

RELATED APPLICATIONS

This application is also related to U.S. Provisional Patent Application No. 62/007,312, filed on Jun. 3, 2014, titled "Nanoparticle Analyzer," the disclosure of which is herein incorporated by reference in its entirety, and U.S. patent application Ser. No. 14/730,138, filed on Jun. 3, 2015, titled "Nanoparticle Analyzer," the disclosure of which is herein incorporated by reference in its entirety.

BACKGROUND

Nanoparticles are ubiquitous and by far the most abundant particle-like entities in natural environments on Earth and are widespread across many applications associated with human activities. There are many types of naturally occurring nanoparticles and man-made (engineered) nanoparticles. Nanoparticles occur in air, aquatic environments, rain water, drinking water, bio-fluids, pharmaceuticals, drug delivery and therapeutic products, and a broad range of many industrial products. Nanoparticles usually occur within polydisperse assemblages, which are characterized by co-occurrence of differently-sized particles.

Given the widespread usage of nanoparticles, the ability to control and accurately characterize their properties may be useful to many applications. Conventional methods for measuring nanoparticle properties may be inaccurate for polydisperse samples of mixed nanoparticle sizes, which are common in many applications. Some of these conventional approaches make measurements on an ensemble of a large number of nanoparticles within a sample. Because the light scattered from all nanoparticles is measured simultaneously, it may be difficult to resolve the nanoparticles into their constituent sizes when there is a range of particle sizes. Other approaches fail to account for the large differences in the intensity of scattered light produced by differently-sized nanoparticles across the range of nanoparticle sizes. In these approaches, the low scattering signals from small nanoparticles may be undetected, or the high scattering signals from larger nanoparticles can obscure the signals from smaller nanoparticles. As a result of these deficiencies, the concentration of nanoparticles of any given size, and hence the entire size distribution, can be subject to unknown error.

These methods of detecting nanoparticles are commonly referred as dark field microscopy. The instrument to perform such an analysis typically comprises a small cell (for example a cuvette) that enables illumination of a liquid with a precisely-defined, narrow light sheet and observation of scattered light from the nanoparticles, usually at a 90-degree angle relative to the light sheet plane. In other words, the direction of observation is perpendicular to the direction of the plane of illumination. Different sizes of particles can be visualized via the camera capturing light scattered by particles, with images having different sizes and intensities (various brightness of pixels) depending on the size of the particles. But as noted above, recording images of light scattered by particles of mixed sizes coexisting in a solution remains somewhat problematic due to the huge difference in the amount of light scattered by particles of different sizes. Specifically, the intensity of scattered light depends very strongly on particle size, changing by many orders of magnitude between 10 nm and 1000 nm diameter nanoparticles, for instance. This problem is also encountered in other areas of photography and videography and is commonly called High Dynamic Range (HDR) imaging. What has been needed is an improved system and method that overcomes the problems that tend to be inherent in dark field microscopy systems.

In U.S. Published Patent Application No. 2015/0346076 A1 to Stramski et al., published Dec. 3, 2015 ("Stramski"), the entirety of which is incorporated herein by reference, these problems were addressed by using several light sources and a single color camera recording simultaneously several different colors of scattered light by the Bayer pattern of pixels corresponding to the three additive primary colors conventionally used in photography. In the Stramski approach, final images were obtained from a single recording device and hence images of the same colloidal volume at different colors were recorded in the same area of the recording device or sensor, thereby resulting in pixel numbering relative to a single point of origin, usually being one of the corners of a sensor in the camera. This made processing images in different colors possible because positions of observed particles were given in the same system of coordinates. However, when multiple sensors are used, the images may become unaligned relative to each other, and Stramski did not address alignment.

What is needed, therefore, is an improved system that overcomes or avoids the alignment problems presented by using multiple detectors that cannot easily be aligned to the exact same point.

SUMMARY

The apparatus, systems, and methods described herein elegantly provide the benefits of simultaneous multi-spectral analysis in the Stramski system with a novel optical configuration that also provides other improvements and benefits such as automated calibration of the volume of investigation as will be apparent to persons of skill in the art. Provided in various example embodiments are apparatus, systems, and methods using a plurality of light sources and a plurality of greyscale cameras to simultaneously record different intensities of light scattered by various particles at different wavebands. Using the apparatus, systems, and methods herein, one may accurately and precisely select the same region of interest (ROI) on all cameras, thus allowing for simultaneous recording of light scattered from exactly the same volume of illuminated sample, with the numbering of pixel coordinates related by known values in both directions, which is important when counting nanoparticles in order to determine their concentration in a colloid.

Accordingly, provided in various example embodiments are apparatus, systems, and methods for detecting electromagnetic radiation of multiple wavelengths (10), examples of which may comprise: a first light source (15) constructed to emit a first beam of electromagnetic radiation at substantially a first wavelength (20); a second light source (25) constructed to emit a second beam of electromagnetic radiation at substantially a second wavelength (30); a combining structure (35) that merges the first and second beams into a combined beam (40), wherein the combined beam is directed at a specimen chamber (50), the chamber is constructed to allow a portion of the combined beam (40) to scatter the electromagnetic radiation in a direction perpendicular (55) to the combined beam (40). The specimen chamber (50) may further comprise a calibration mask (95), the mask including at least two calibration marks (100), with a calibration light source (110) constructed to emit a calibration beam (112) of electromagnetic radiation comprising the first and second wavelengths, wherein the calibration light source (100) directed at the calibration mask (95) emits its beam (112) parallel to the scattered portion of the combined beam (55). Then, the scattered portion of the combined beam (55) and the calibration beam (112) may be directed to a decombining (splitting) structure (65) that separates the electromagnetic radiation into the first wavelength radiation (70) and the second wavelength radiation (80). The separated first wavelength radiation (70) is directed to a first sensor (75) biased to detect electromagnetic radiation at substantially the first wavelength; the separated second wavelength radiation (80) is detected by a second sensor (85) biased to detect electromagnetic radiation at substantially the second wavelength; a processor (87) is connected to the first (75) and second (85) sensors, the processor (87) being configured to perform the following steps: when the calibration light source (110) is actuated, obtaining a first calibration image (115) from the first sensor (75) and a second calibration image (120) from the second sensor (85); detecting the calibration marks (100) from the calibration mask (95) in the first calibration image and in the calibration second image; determining a calibration correction (125, 130) based of the location of the calibration marks (100) in the first calibration image and the location of the calibration marks (100) in the second calibration image; when the first (15) and second (25) light source are actuated, obtaining a first detection image from the first sensor (75) and a second detection image from the second sensor (85); adjusting the detection images relative to each other based on the calibration correction (125, 130).

In various example embodiments the processor may count the number of particles on the merged image after adjusting the images relative to each other. In various example embodiments the first and second light sources may be lasers. In various example embodiments the calibration mask may comprise a plate (105) that is transparent to the first and second wavelengths, and the calibration marks (100) may be opaque to the first (70) and second (80) wavelengths. In various example embodiments either one or both of the combining structure (35) and the decombining structure (65) may be a dichroic mirror. In various example embodiments the system may further comprise a light sheet former (45) that forms the combined beam (40) into a sheet of electromagnetic radiation, and that sheet may be directed at the specimen chamber (50). In various example embodiments the system may further comprise an imaging objective (60) that focuses the scattered beam (55) on the first and second sensors via the decombining structure (65). In various example embodiments the position of the decombining structure (65) can be adjusted (67) to change the direction of the separated second wavelength radiation (80) relative to the second sensor (85). In various example embodiments the position of the second sensor can be adjusted (90). In various example embodiments the processor (87) may determine the calibration correction (125, 130) by: aligning the calibration marks (100) from the first image to the second image; determining a rotational shift phi φ (125) between the first and second images; and determining a translational delta x and delta y (130) between the first and second images. In various example embodiments the processor (87) may be connected to the first (15) and second (25) light sources and the calibration light source (110), and the processor (87) may perform the following steps: actuating the calibration light source (110) prior to determining the calibration correction (125, 130); and actuating the first (15) and second (25) light sources prior to obtaining an image from the first sensor (115) and second sensor (120). In various example embodiments the decombining structure (65) may be connected to an electro-mechanical adjustor (67) that can change the position of the decombining structure (65), the adjustor (67) may be connected to the processor (87), and the processor (87) may actuate the adjustor (67) to determine the calibration correction (125, 130). In various example embodiments the second sensor (85) may be connected to an electro-mechanical adjustor (90) that can change the position of the second sensor (85), the adjustor (90) may be connected to the processor (87), and the processor (87) may actuate the adjustor (90) to determine the calibration correction (125, 130).

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

BRIEF DESCRIPTION OF THE DRAWINGS

The invention can be better understood with reference to the following figures. The components within the figures are not necessarily to scale, emphasis instead being placed on clearly illustrating example aspects of the invention. In the figures, like reference numerals designate corresponding parts throughout the different views and/or embodiments. It will be understood that certain components and details may not appear in the figures to assist in more clearly describing the invention.

DETAILED DESCRIPTION

Figure 1:
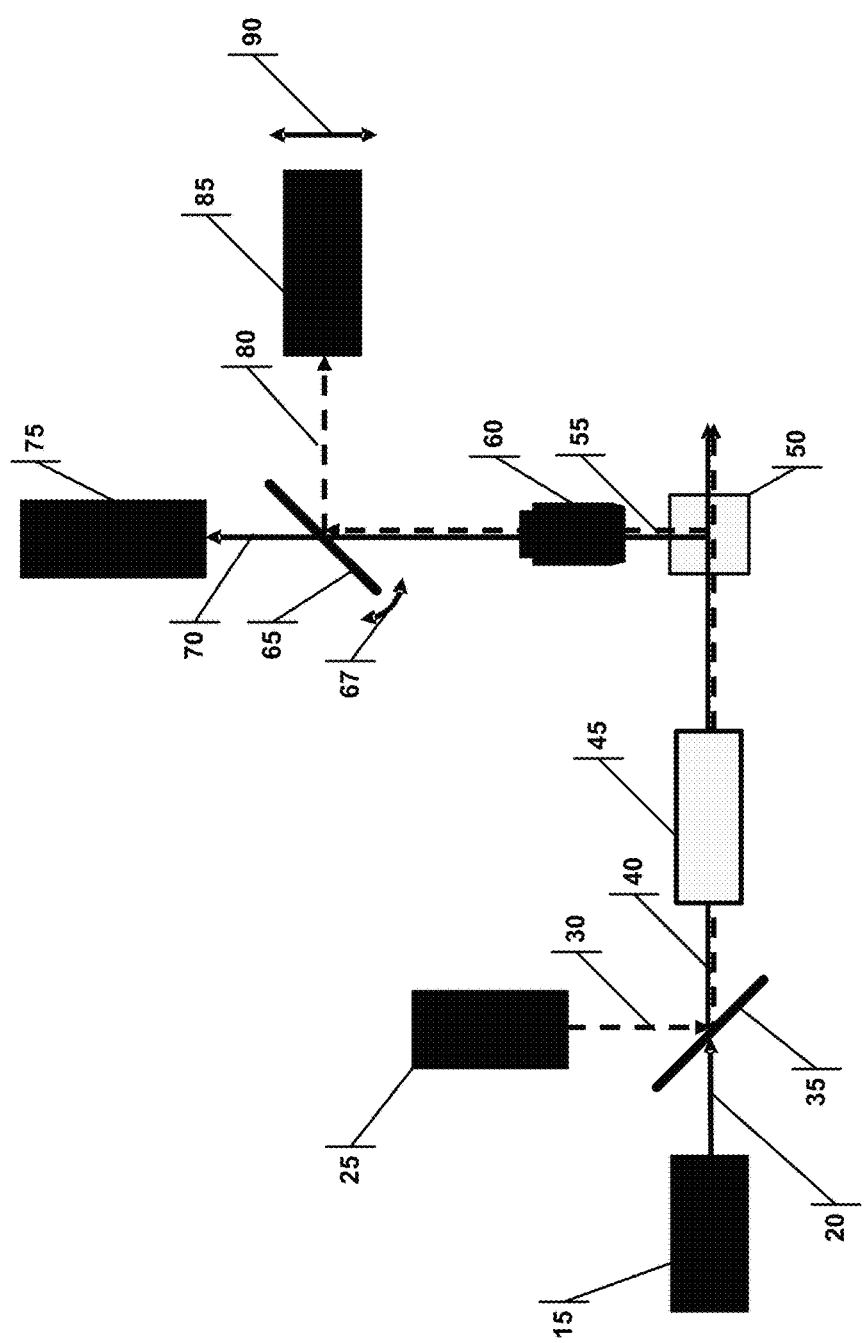
FIG. 1 illustrates a system for detecting electromagnetic radiation of multiple wavelengths.

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in the singular form for clarity. However, it should be noted that some embodiments include multiple iterations of a technique or multiple mechanisms unless noted otherwise. Similarly, various steps of the methods shown and described herein are not necessarily performed in the order indicated, or performed at all in certain embodiments. Accordingly, some implementations of the methods discussed herein may include more or fewer steps than those shown or described. Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

The following list of example features corresponds with FIGS. 1-4 and is provided for ease of reference, where like reference numerals designate corresponding features throughout the specification and figures:

A system for detecting electromagnetic radiation of multiple wavelengths 10.
An alternate system for detecting electromagnetic radiation of multiple wavelength 10A.
First light source at a first wave length 15.
First beam of electromagnetic radiation at substantially a first wavelength 20.
Second light source at a second wavelength 25.
Second beam of electromagnetic radiation at substantially a second wavelength 30.
A third light source at a third wave length 32.
Third beam of electromagnetic radiation at substantially a third wavelength 34.
Combining structure/dichroic mirror 35.
A second combining structure/dichroic mirror 37.
Combined beam 40.
Light sheet former 45.
Specimen chamber/cuvette 50.
A portion of the third beam that scatters 55.
Imaging objective 60.
Decombining structure/dichroic mirror 65.
Rotation by an electromechanical adjustor 67.
Separated first wavelength radiation 70.
First sensor biased to detect electromagnetic radiation at substantially the first wave length 75.
Separated second wavelength radiation 80.
Second sensor biased to detect electromagnetic radiation at substantially the second wave length 85.
Separated third wavelength radiation 86.
Processor 87.
Second decombining structure/dichroic mirror 88.
Third sensor biased to detect electromagnetic radiation at substantially the third wave length 89.
Movement of sensor by electromechanical adjustor 90.
Calibration mask 95.
Calibration marks 100.
Transparent portion of calibration mask 105.
Calibration light source 110.
Calibration beam 112.
First calibration image 115.
Second calibration image 120.
Rotational shift phi $\phi$ 125.
Translational shift (or delta) X and delta Y 130.
Region of interest (ROI) and merged image 135.
Third calibration image 140.
Second rotational shift phi $\phi_2$ 145.
Second translational shift (or delta) $X_2$ and delta $Y_2$ 150.

With reference to FIG. 1, in various example embodiments the apparatus, systems, and methods for detecting electromagnetic radiation of multiple wavelengths may comprise a first light source at a first wave length 15 and a second light source at a second wavelength 25, such as two lasers with different beam colors or wavelengths. Each of these two beams is directed at a combining structure 35, such as a dichroic mirror, which combines the beams from light sources 15, 25 into a single combined beam 40 and directs the combined beam 40 to an optical system such as a light sheet former 45. The light sheet former 45 may comprise a cylindrical lens with long working distance objective that forms a very narrow sheet of illumination. The light sheet may be directed to a transparent specimen chamber 50 (such as a cuvette) that houses a colloid containing particles, i.e. nanoparticles (not shown). A portion of the combined beam that scatters 55 upon impacting the particles present in the colloid solution contained within the cuvette 50 has the same wavelengths as the illuminating light from the light sheet former 45, and can typically be observed at 90-degree angle by focusing an imaging objective 60, such as a microscope equipped with another long working distance objective. The scattered light exiting the imaging objective 60 is split into constituent wavelengths at a decombining structure 65 such as a second dichroic mirror, namely the separated first wavelength radiation 70 and the separated second wavelength radiation 80, that may independently reach the two sensors 75, 85 (such as those disposed within digital grey-scale cameras), attuned to detect electromagnetic radiation at substantially the first and second wave lengths 15, 25, respectively. The system can be easily extended into more wavelengths and more corresponding sensors 75, 85 by adding more pairs of appropriate dichroic mirrors 35, 65 to combine and split more wavelengths of illuminating light sources 15, 25. Such an example is shown in FIG. 3B, which illustrates a three wavelength system with a third light source at a third wave length 32, that produces a third beam of electromagnetic radiation at substantially a third wavelength 34, and a second combining structure/dichroic mirror 37. On the detection side of the system 10A, a second decombining structure/dichroic mirror 88 separates a third wavelength radiation 86, so that it can be detected by a third sensor biased to detect electromagnetic radiation at substantially the third wave length 89.

Figure 3A:
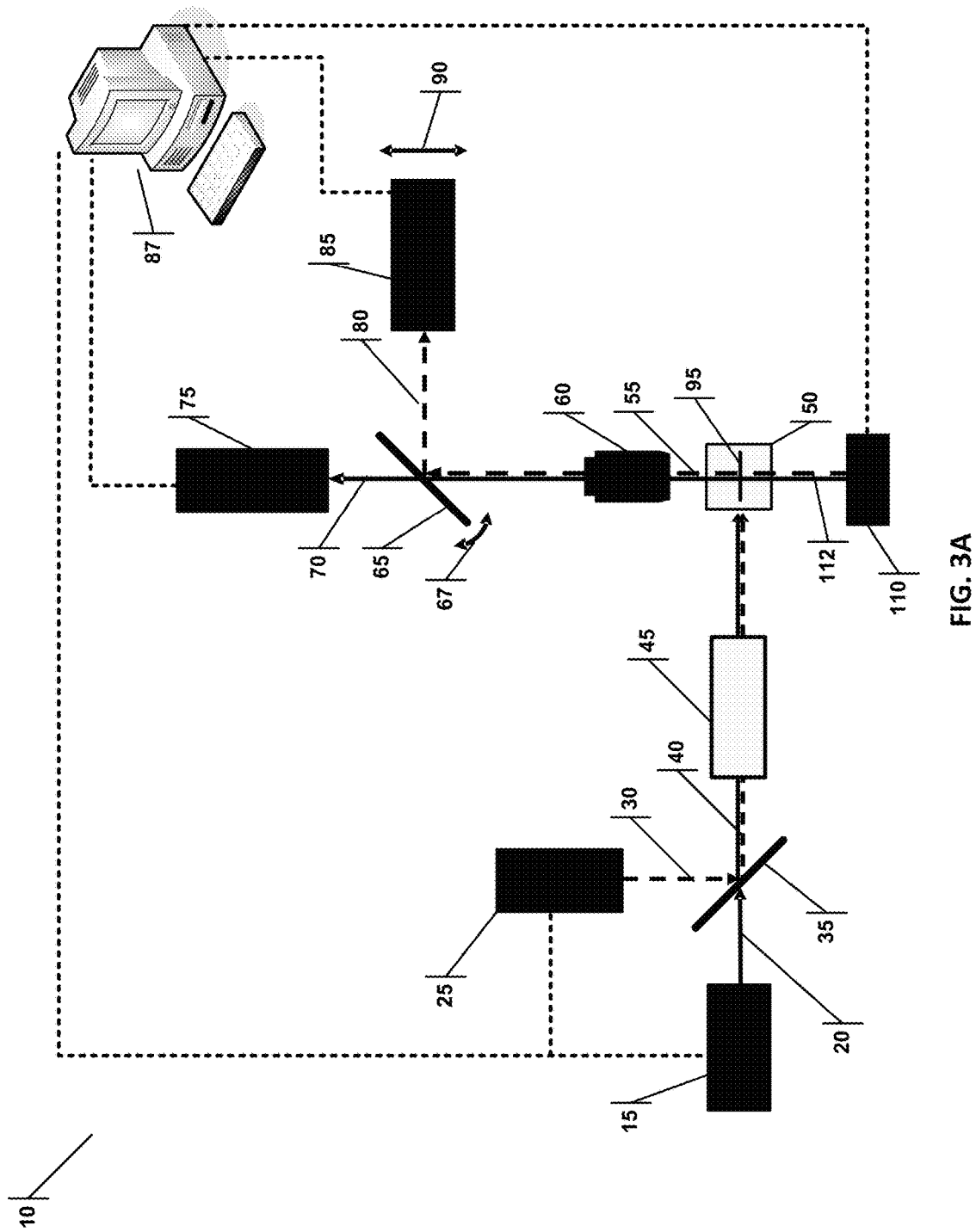
FIG. 3A illustrates a system for detecting electromagnetic radiation of two wavelengths using a calibration mask and a calibration light source.
Figure 3B:
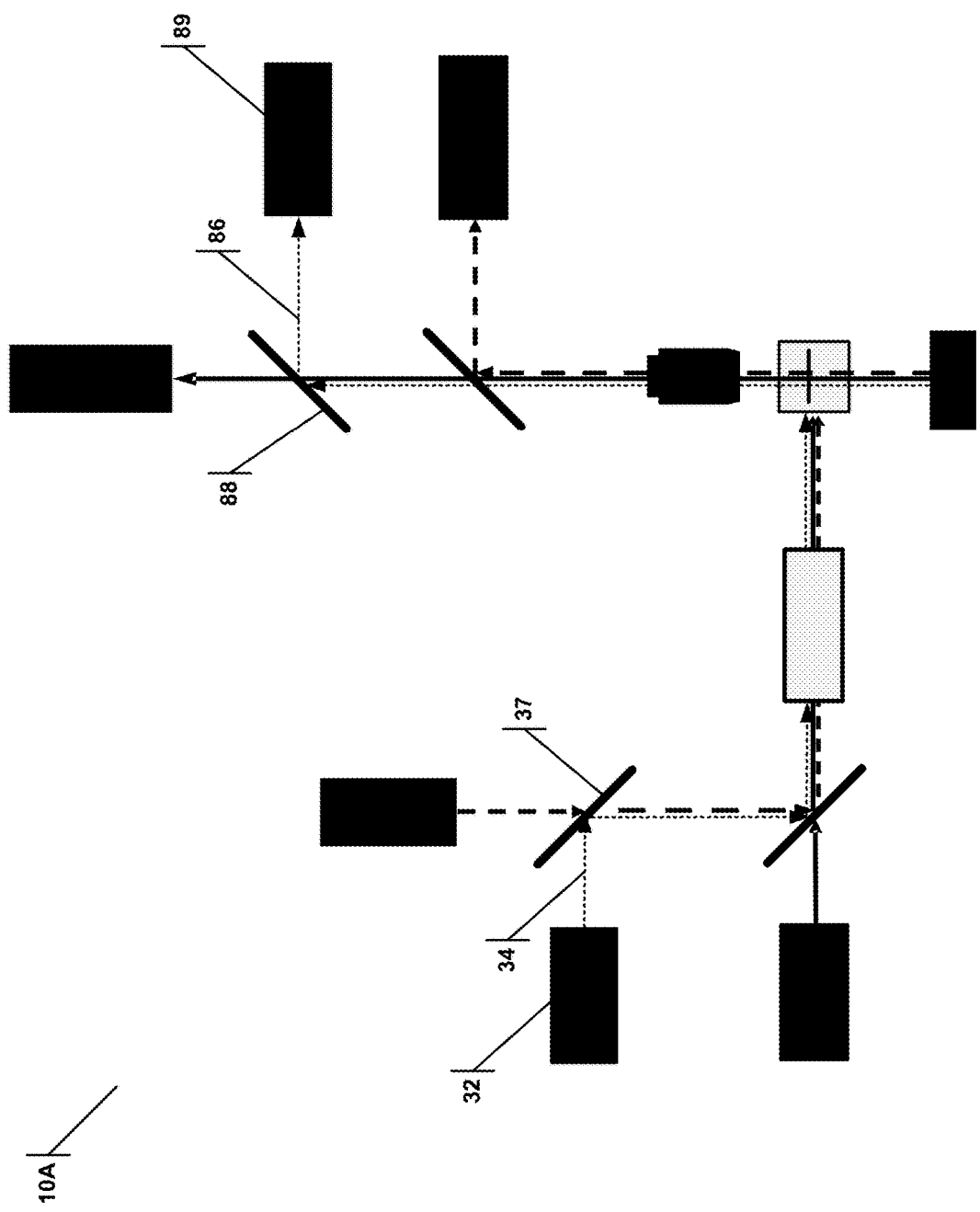
FIG. 3B illustrates a system for detecting electromagnetic radiation of three wavelengths using a calibration mask and a calibration light source.

The decombining structure 65 may be moveable (for instance, it may be tilted along an axis perpendicular to the line of sight), as illustrated in FIG. 3A. The viewing area of the second sensor 85 can be changed in relation to that of the first sensor 75, for instance via rotation by an electromechanical adjustor 67. A similar result can be obtained by moving the second sensor 85 perpendicularly to the direction of split imaging light beam 80, for instance by an electromechanical adjustor 90. However, these methods, being mechanical in nature, might not achieve the accuracy desired. For example, typical digital sensors have pixels that are squares with sides 5 micrometers long. Hence, to get positioning of a given image space point within 1-pixel accuracy, one would need to move second sensor 85 with less than 5 micrometers absolute accuracy in two directions, or tilt the mirror by much less than a one-degree angle. This accuracy may be hard to obtain and reliably maintain for extended periods of time.

Figure 2:
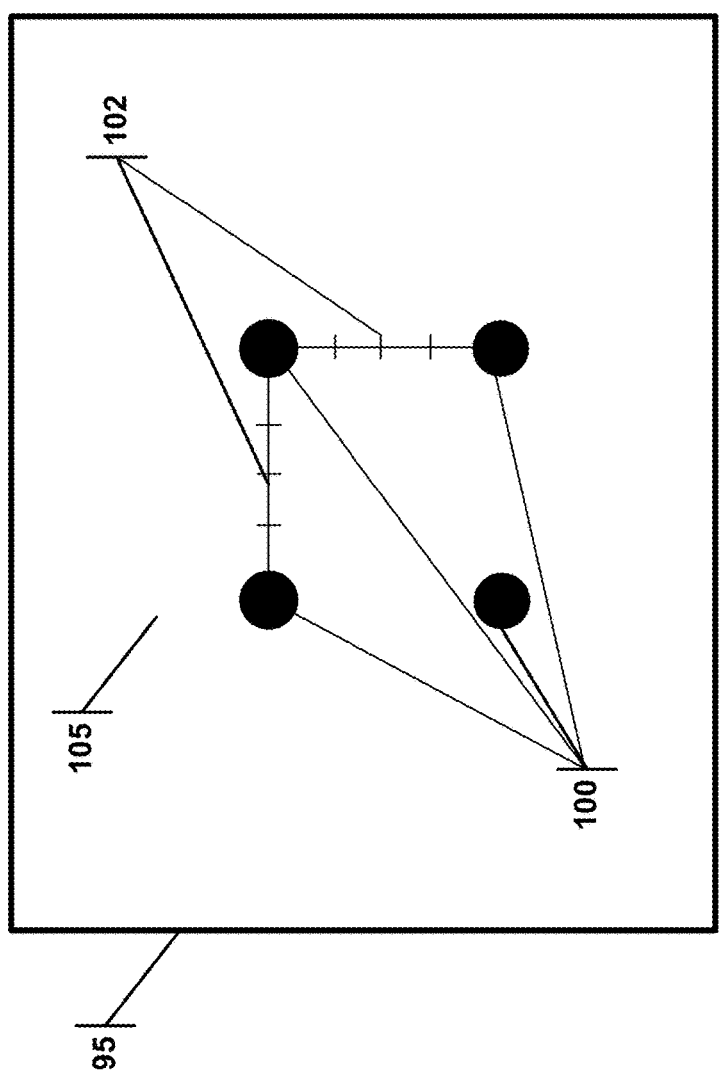
FIG. 2 illustrates a calibration mask.

Other various example embodiments may be employed that tend to overcome the limitations of mechanical methods. For example, with reference to FIGS. 2-6, various example embodiments may use a special calibration mask 95 to precisely position the image from one sensor 75 in relation to the other sensor 85 electronically. The calibration mask 95 may be made from glass or another transparent material, with several micro-points or calibration marks 100 etched or painted on its transparent surface 105, as shown in FIG. 2. Using more than two calibration marks may render the final calibration more accurate and easier to implement. In the non-limiting example shown in FIG. 2, the calibration marks 100 are arranged in a rectangular pattern, but a triangular pattern or any other multi-point pattern could be just as effective. The calibration mask 95 may also have a calibration scale 102. This can be helpful if the sensors are not perpendicular to the incoming beams 70, 80. If this happens, then each sensor 75, 85 may have a slightly different number of length units per pixel (usually measured in nm/pixel). By adding two perpendicular calibration scales 102 between calibration marks 100, the processor 87 can effectively account for this difference and enable the calibration of the field of view of each sensor 75, 85 separately and accurately. In fact, such scales enable calibration of any sensor that is being used in the system, even if they are not same or with an unknown size of a pixel, giving precise calibration of the viewable area on both sensors in units of length instead of pixels. As yet another alternative, the processor 87 may simply be programmed to know that the calibration mask 95 has, for example in FIG. 2, four calibration marks 100, and may further know the relative distances between the marks. In this latter alternative, the mask 95 need not contain the calibration scale, and based on the preprogramed lengths, the processor 87 can may the appropriate adjustments to arrive at an appropriate calibration correction.

Such a calibration mask 95 may be placed within the specimen chamber 50 and may either be illuminated by the scattered beam 55, formed when the light sheet formed via the combining structure 35 and the light sheet former 45 encounters the particles in the colloid solution contained within the specimen chamber 50, or by a calibration beam 112 emitted by a calibration light source 110, as shown in FIG. 3A. Thus, when an image is captured by the sensor 75 or by the sensor 85, the four points made on the image from the calibration marks 100 on the transparent plate 105 of the calibration mask 95 define a rectangular area smaller than those areas that are recorded by the sensors and that could be encompassed wholly by both sensors 75, 85. Computer-detected images of points from the calibration plate or mask 95 define the very same area on both sensor images with a single-pixel or even sub-pixel accuracy. This highly accurate limitation (by design) of the ROI 135 ensures that each sensor will be simultaneously examining exactly the same region of the sample. FIG. 3B illustrates a system employing three wavelengths of light. At this point, it may be necessary to adjust one or both calibration images such that the calibration marks 100 detected in each calibration image are in the same scale as each other. This is the scale adjustment and may be performed by using the calibrations scales 102, and/or by the processor 87 being preprogramed to know the relative distances between the calibration marks 100.

Figure 4A:
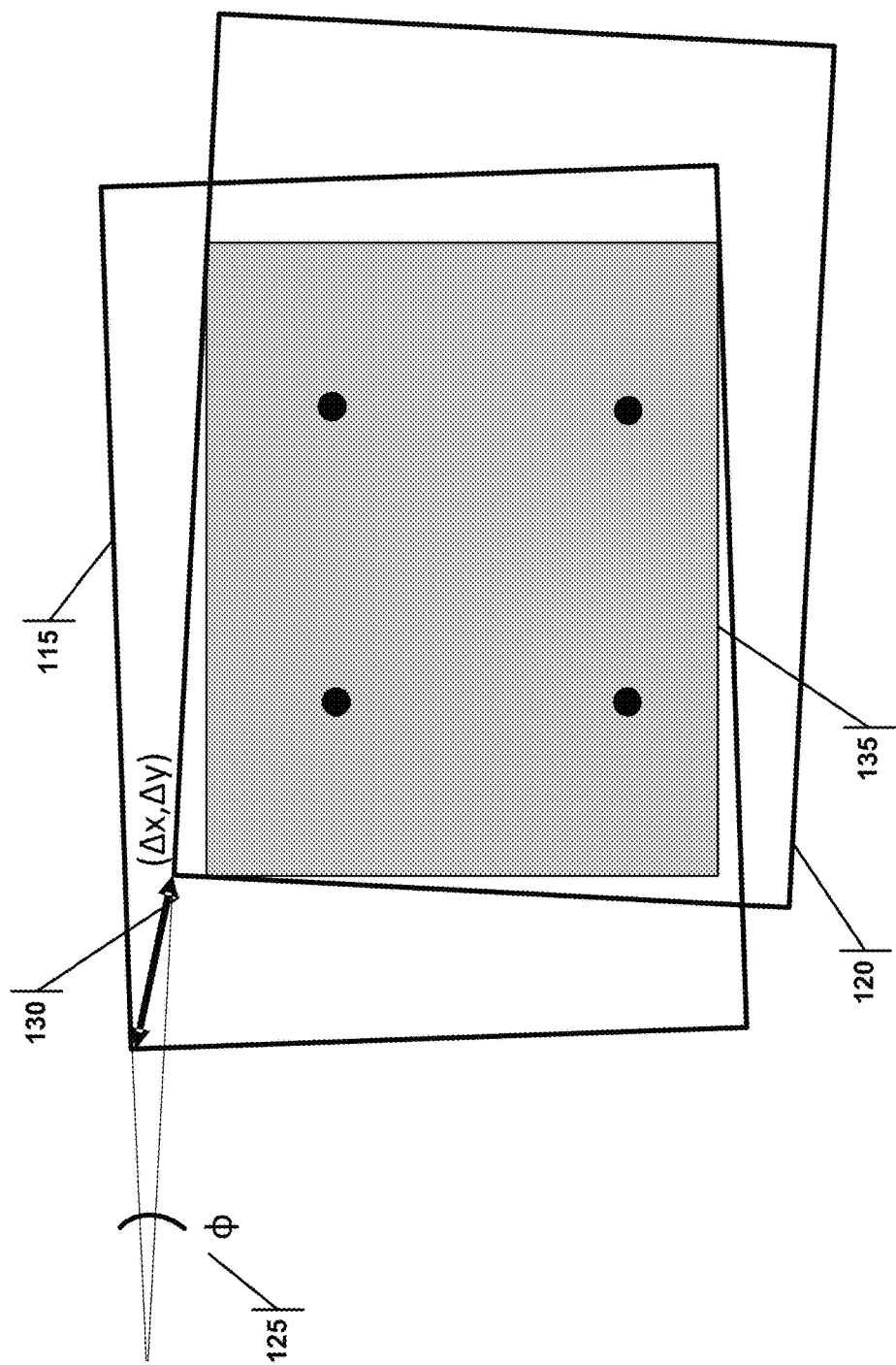
FIG. 4A illustrates the alignment of the calibration marks from two separate images.
Figure 4B:
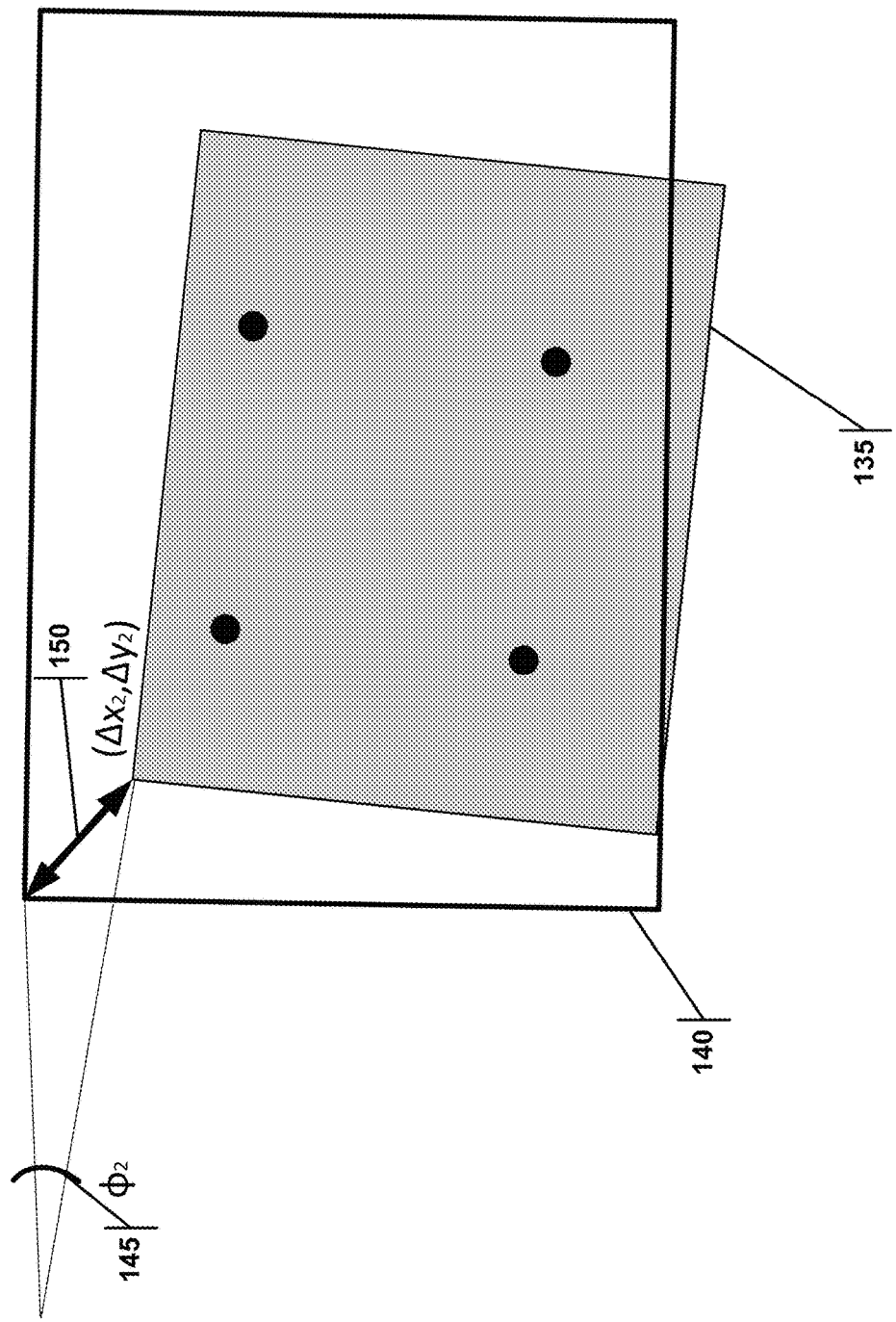
FIG. 4B illustrates the alignment of the calibration marks from the merged image of FIG. 4A and a third calibration image.

By applying simple mathematical expressions relating pixel shifts between two or more images, one can relate the absolute positions of recorded images of light scattered by particles, thus ensuring counting and tracking of the same particles on different images. This is the translational/rotational shift. More specifically, the mathematical relationship of pixel shifts between two or more images can be expressed as:

$$x' = x \cos \phi + y \sin \phi + \Delta x \quad \text{Equation (1)}$$

$$y' = -x \sin \phi + y \cos \phi + \Delta y \quad \text{Equation (2)}$$

where (x, y) are the pixel numbers (coordinates) in two directions on one sensor 75 and (x', y') are the coordinates on the second sensor 85 with a translational shift (or delta) between the two images of ($\Delta x$, $\Delta y$) 130 and a rotational shift or tilt of angle $\phi$ 125, as shown in FIG. 4A. Therefore, the calibration correction may include a scale adjustment, a translational shift and a rotational shift. In some embodiments it may be preferable to use more than two calibration marks (such as three calibration marks as shown in FIGS. 4A and 4B), which would allow the system and method to more accurately identify and compare the marks between the images.

The above listed values of shift and tilt between two images (115 and 120 in FIG. 4A) can be easily derived from geometrical positions of the ROI 135 corners and edges on the different images, which can be precisely determined by the computer detection software that is used for tracking particles on the recorded images. FIG. 4B illustrates this same method used to align the calibration marks with the third calibration image 140, using a second rotational shift phi $\phi_2$ 145 and a second translational delta $x_2$ and delta $y_2$ 150. The aligned image from FIG. 4A—i.e., the ROI 135 aligning the first and second calibration images (135, 145)—is then aligned to the third calibration image 140. This same technique can be used to align additional calibration images at different wavelengths.

Figure 5:
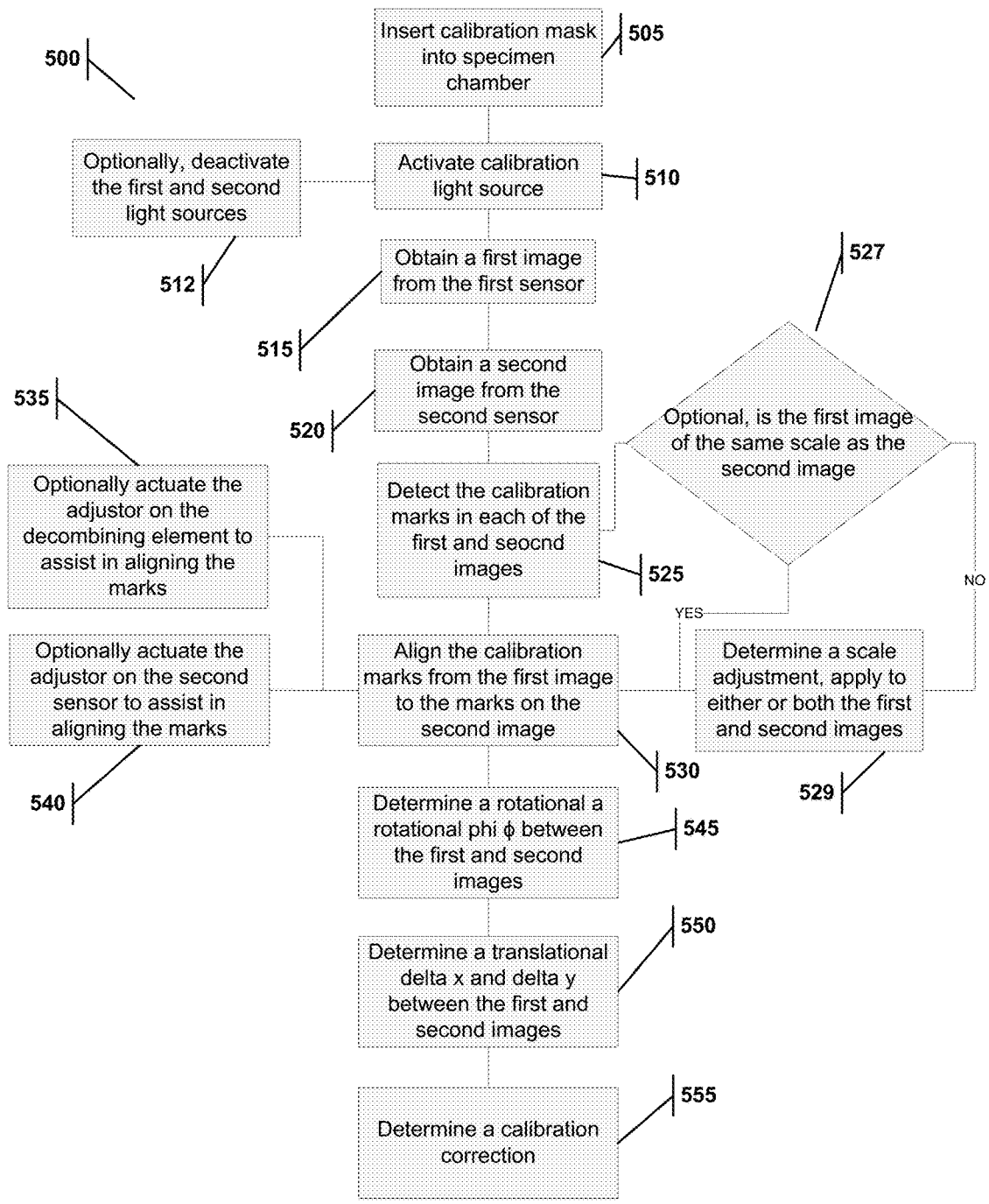
FIG. 5 is a flow chart detailing a method of determining a calibration correction in a system for detecting electromagnetic radiation of multiple wavelengths.

FIG. 5 enumerates steps of the method 500 by which the calibration correction (pixel shifting) may be determined accurately. In a first step 505, the calibration mask 95 may be inserted into the specimen chamber 50. Then, in step 510, the calibration light source 110 is activated. Step 512, wherein the first light source 15 and the second light source 25 are deactivated, can be optionally performed simultaneously with 510. With the calibration light source 110 on from step 510, a first image is obtained from the first sensor 75 in step 515. A second image is obtained from the second sensor 85 in step 520. Now with these two images captured from the calibration beam 112, in step 525 the calibration marks 100 are detected in each image. The processor 87 may optionally make a scale adjustment by first determining whether there is a difference in scale between the images at step 527. If there is, then the scale adjustment is determined at step 529.

In the next step, 530, the processor 87 aligns the calibration marks 100 from the first image with the calibration marks 100 on the second image by calculating pixel coordinates of each of the points from the calibration marks 100 in each of the images and calculating the translation of these points. Optionally, in place of step 530 or as part of step 530, the processor 87 may facilitate alignment of the first image 115 with the second image 120 using the corners of the ROI 135 by actuating the rotational electromechanical adjustor 67 on the decombining element 65 to assist in aligning the marks 100, as in step 535, or by actuating the translational electromechanical adjustor 90 on the second sensor 85 to assist in aligning the marks 100, as in step 540. Because the rotational electromechanical adjustor 67 may be connected to the processor 87 and may in fact be actuated by the processor 87, the processor 87 may directly know the rotation shift ϕ needed to shift the first calibration image to align it with the second calibration image, and vice versa. Equivalently, by keeping track of how many pixels or how much distance the translational electromechanical adjustor 90 (also actuated by the processor 87) had to move the sensor 85 to align the images, the processor 87 may directly know the translational shift.

Figure 6:
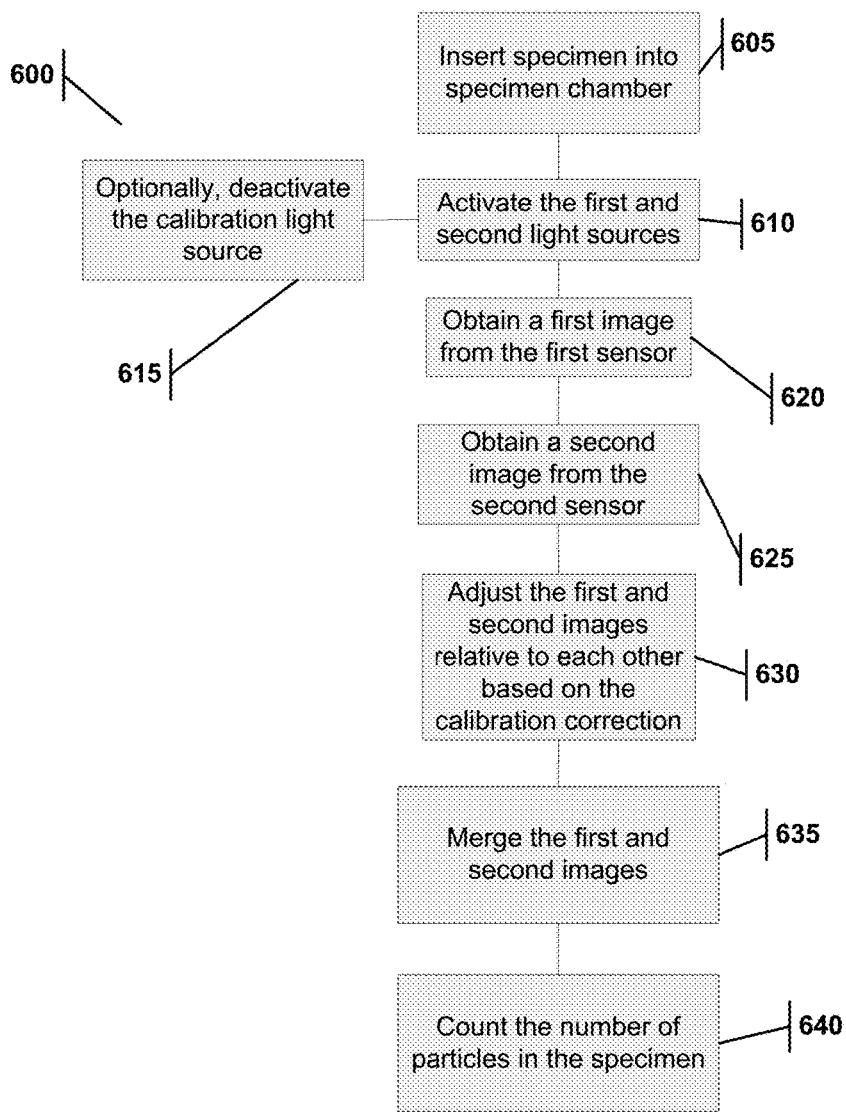
FIG. 6 is a flow chart detailing a method of applying a calibration correction in a system for detecting electromagnetic radiation of multiple wavelengths.

Based on the adjustments required in step 530 to align the marks 100 and thereby the ROI 135 between the two images, the rotational shift ϕ between the images can be determined (step 545), as well as the translational delta x and delta y between the images (step 550). By combining the information from steps 545 and 550, the calibration correction of step 555 may be expressed through equations (1) and (2). This calibration correction may then be used to process images taken by the same sensors 75 and 85, to identify duplicated particles detected and remove them from the tally, providing an accurate and reproducible estimation of the examined colloid volume. With more accurate particle tallies taken from an accurately defined corresponding colloid volume, the concentration of particles can be easily and effectively determined. Note that the calibration can be applied or performed after the specimen has been imaged—i.e., the calibration correction can be applied to the video and then processed. Also note that if the processor 87 determined that a scale adjust was necessary in steps 527 and 529, then the images would also be adjusted by the scale adjustment when taking the particle count. FIG. 6 illustrates the steps of the method 600 applying the calibration correction on images. After there is a specimen placed in the chamber 50, (step 605), then the first and second light sources, 15 and 25 respectively, can be activated (step 610). It may optionally be desirable at this point to simultaneously deactivate the calibration light source 110, as shown in step 615. A first image is obtained from the first sensor 75 (step 620), and a second image is obtained from the second sensor 85 (step 625). Then, in step 630, the first and second images can be adjusted relative to each other based on the calibration correction. Thus the first and second images can be merged (635) so that duplicate particles may be identified. Then, the number of particles in the specimen can be counted more accurately (step 640).

Although exemplary embodiments and applications of the invention have been described herein including as described above and shown in the included example Figures, there is no intention that the invention be limited to these exemplary embodiments and applications or to the manner in which the exemplary embodiments and applications operate or are described herein. Indeed, many variations and modifications to the exemplary embodiments are possible as would be apparent to a person of ordinary skill in the art. The invention may include any device, structure, method, or functionality, as long as the resulting device, system or method falls within the scope of one of the claims that are allowed by the patent office based on this or any related patent application.

The invention claimed is:

1. A system for emitting and detecting electromagnetic radiation of multiple wavelengths to observe particles in a polydisperse solution, the system comprising:
   a first light source constructed to emit a first beam of electromagnetic radiation at substantially a first wavelength;
   a second light source constructed to emit a second beam of electromagnetic radiation at substantially a second wavelength;
   a combining structure that merges the first and second beams into a combined beam, wherein the combined beam is directed at a specimen chamber, the chamber is constructed to allow a portion of the combined beam to scatter perpendicular to the combined beam;
   the specimen chamber further comprising a calibration mask, the mask including at least two calibration marks;
   a calibration light source constructed to emit a calibration beam of electromagnetic radiation comprising the first and second wavelengths, the calibration light source directed at the calibration mask parallel to the scattered portion of the combined beam;
   the scattered portion of the combined beam and the calibration beam directed to a decombining structure that separates the electromagnetic radiation into a separated first wavelength radiation and a separated second wavelength radiation;
   the separated first wavelength radiation directed to a first sensor biased to detect electromagnetic radiation at substantially the first wave length;
   the separated second wavelength radiation directed to a second sensor biased to detect electromagnetic radiation at substantially the second wave length;
   a processor connected to the first and second sensors, the processor configured to perform the following steps:
      when the calibration light source is actuated:
         obtaining a first calibration image from the first sensor and a second calibration image from the second sensor;
         detecting the calibration marks from the calibration mask in the first calibration image and in the second calibration image;
         determining a calibration correction based on the location of the calibration marks in the first calibration image and the location of the calibration marks in the second calibration image;
      when the first and second light source are actuated:
         obtaining a first detection image from the first sensor and a second detection image from the second sensor;
         adjusting the detection images relative to each other based on the calibration correction.

2. The system of claim 1, wherein the processor is configured to count the number of particles on a merged image formed by adjusting the detection images relative to each other based on the calibration correction.

3. The system of claim 1, wherein the first and second light sources are lasers.

4. The system of claim 1, wherein the calibration mask comprises a plate that is transparent to the first and second wavelengths, and wherein the calibration marks are opaque to the first and second wavelengths.

5. The system of claim 1, wherein either one or both of the combining structure and the decombining structure is a dichroic mirror.

6. The system of claim 1, further comprising a light sheet former that forms the combined beam into a sheet of electromagnetic radiation directed at the specimen chamber.

7. The system of claim 1, further comprising an imaging objective that focuses the first and second wavelengths on the first and second sensors.

8. The system of claim 1, wherein the position of the decombining structure can be adjusted rotationally to change the direction of the separated second wavelength radiation relative to the second sensor.

9. The system of claim 1, wherein the position of the second sensor can be adjusted.

10. The system of claim 1, wherein the processor determines the calibration correction by:
   aligning the calibration marks from the first calibration image to the second calibration image;
   determining a rotational shift phi $\phi$ between the first and second calibration images; and
   determining a translational delta x and delta y between the first and second calibration images.

11. The system of claim 10, wherein prior to aligning the calibration marks, the processor calculates a scale adjustment based on the difference in scale between the first and second calibration images.

12. The system of claim 11, wherein the calibration mask has a calibration scale, and the scale calculation is based on the calibration scale.

13. The system of claim 11, wherein the processor is preprogramed with the relative distances between the calibration marks, and the scale calculation is based on the preprogramed relative distances.

14. The system of claim 1, wherein the processor is connected to the first and second light sources and the calibration light source, and the processor performs the following steps:
   actuating the calibration light source prior to determining the calibration correction; and
   actuating the first and second light sources prior to obtaining a detection image of the specimen in the specimen chamber from the first sensor and the second sensor.

15. The system of claim 1, wherein the decombining structure is connected to an electromechanical adjustor that can change the position of the decombining structure, and the adjustor is connected to the processor, and the processor performs the following steps:
   actuating the adjustor to determine the calibration correction.

16. The system of claim 1, wherein the second sensor is connected to an electro-mechanical adjustor that can change the position of the second sensor, the adjustor is connected to the processor and the processor performs the following steps:
   actuating the adjustor to determine the calibration correction.

17. A method of detecting electromagnetic radiation of multiple wavelengths, the method comprising the steps of:
   providing a system for detecting electromagnetic radiation of multiple wavelengths, the system comprising:
      a first light source constructed to emit a first beam of electromagnetic radiation at substantially a first wavelength;
      a second light source constructed to emit a second beam of electromagnetic radiation at substantially a second wavelength;
      a combining structure that merges the first and second beams into a combined beam, wherein the combined beam is directed at a specimen chamber, and wherein the chamber is constructed to allow a portion of the combined beam to scatter perpendicular to the combined beam;
      the specimen chamber further comprising a calibration mask, the mask including at least two calibration marks;
      a calibration light source constructed to emit a calibration beam of electromagnetic radiation comprising the first and second wavelengths, the calibration light source directed at the calibration mask parallel to the scattered portion of the combined beam;
      the scattered portion of the combined beam and the calibration beam directed to a decombining structure that separates the electromagnetic radiation into the separated first wavelength radiation and the separated second wavelength radiation, wherein the separated first wavelength radiation is directed to a first sensor biased to detect electromagnetic radiation at substantially the first wave length, and wherein the separated second wavelength radiation is detected by a second sensor biased to detect electromagnetic radiation at substantially the second wave length; and
      a processor connected to the first and second sensors;
   actuating the calibration light source;
   obtaining a first calibration image from the first sensor and a second calibration image from the second sensor;
   detecting the calibration marks from the calibration mask in the first calibration image and in the second calibration image;
   determining a calibration correction based of the location of the calibration marks in the first calibration image and the location of the calibration marks in the second calibration image;
   actuating the first and second light source;
   obtaining a first detection image from the first sensor and a second detection image from the second sensor; and
   adjusting the detection images relative to each other based on the calibration correction.

18. The method of claim 17, further comprising the steps of:
   counting the number of particles on a merged image after the detected images are adjusted relative to each other.

19. The method of claim 17, wherein the system further comprises a light sheet former that forms the combined beam into a sheet of electromagnetic radiation and that sheet is directed at the specimen chamber, the method further comprising the steps of:
   forming the combined beam into a sheet of electromagnetic radiation; and
   directing that sheet at the specimen chamber.

20. The method of claim 17, wherein the system further comprises an imaging objective that focuses the first and second wavelengths on the first and second sensors, the method further comprising the steps of:
   focusing the first and second wavelengths on the first and second sensors.

21. The method of claim 17, wherein the position of the decombining structure in the system can be adjusted to change the direction of the separated second wavelength radiation relative to the second sensor, the method further comprising the steps of:

adjusting the position of the decombining structure in the system to change the direction of the separated second wavelength radiation relative to the second sensor.

22. The method of claim 17, wherein the position of the second sensor in the system can be adjusted, the method further comprising the steps of:

adjusting the position of the second sensor.

23. The method of claim 17, wherein the processor is constructed to align the calibration marks from the first calibration image to the second calibration image, determine a rotational phi ϕ between the first and second calibration images, and determine a translational delta x and delta y between the first and second calibration images; the method further comprising the steps of:

aligning the calibration marks from the first calibration image to the second calibration image;

determining a rotational shift phi ϕ between the first and second calibration images; and determining a translational delta x and delta y between the first and second calibration images.

24. The method of claim 17, wherein the processor is connected to the first and second light sources and the calibration light source, and the processor is constructed to actuate the calibration light source prior to determining the calibration correction, and actuate the first and second light sources prior to obtaining the detection images from the first sensor and second sensor, wherein the method further comprising the steps of:

actuating the calibration light source prior to determining the calibration correction; and actuating the first and second light sources prior to obtaining the detection images from the first sensor and the second sensor.

25. The method of claim 14, wherein the decombining structure is connected to an electromechanical adjustor that can change the position of the decombining structure, the adjustor is connected to the processor, and the processor is constructed to actuate the adjustor to determine the calibration correction, wherein the method further comprising the steps of:

actuating the adjustor to determine the calibration correction.

26. The method of claim 14, wherein the second sensor is connected to an electromechanical adjustor that can change the position of the second sensor, the adjustor is connected to the processor, and the processor is constructed to actuate the adjustor to determine the calibration correction, and wherein the method further comprising the steps of:

actuating the adjustor to determine the calibration correction.

* * * * *